US00PP15252P2

(12) United States Plant Patent
Olesen et al.

(10) Patent No.: US PP15,252 P2
(45) Date of Patent: Oct. 19, 2004

(54) MINIATURE ROSE PLANT NAMED 'POULHI011'

(50) Latin Name: *Rosa hybrida*
Varietal Denomination: POULhi011

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 8 days.

(21) Appl. No.: 10/738,154

(22) Filed: Dec. 16, 2003

(51) Int. Cl.[7] ..... A01H 5/00
(52) U.S. Cl. ..... Plt./121
(58) Field of Search ..... Plt./121

*Primary Examiner*—Kent Bell
*Assistant Examiner*—S B McCormick-Ewoldt

(57) ABSTRACT

A new miniature rose plant which has abundant, pink flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'POULhi011'.

SUMMARY OF THE INVENTION

The present discovery constitutes a new and distinct variety of a miniature pot rose plant which was discovered in a cultivated area. The mutation resulted from 'POULtipe', a miniature pot rose hybridized by the same inventors. The resulting mutation was selected and evaluations were conducted on the resulting rose plants in a controlled environment. 'POULtipe' is described and illustrated in U.S. Plant patent application Ser. No. 09/287,291 filed Mar. 31, 1999 now abandoned. The new rose variety resulted from a naturally occurring mutation of unknown causation on a branch of 'POULtipe'.

The rose plant of the present discovery has a unique combination of characteristics which are outstanding in the new variety and which distinguish it from the original rose 'POULtipe' as well as all other varieties which we are aware of. For example, the new variety has:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventors, and distinguish 'POULhi011' from all other varieties of which we are aware.

Asexual reproduction of 'POULhi011' by cuttings and traditional budding was first done by L. Pernille and Mogens N. Olesen in their nursery in Fredensborg, Denmark in 1995. This initial and other subsequent propagations conducted in controlled environments have demonstrated that the characteristics of 'POULhi011' are stable and reproduced true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'POULhi011'. Specifically illustrated in the drawing:

FIG. 1.1; Open flower, and cluster of open flowers, showing branching and the attachment of leaves, buds, and peduncles;

FIG. 1.2; Flower bud closed, partially open, and open;

FIG. 1.3; Flower petals, detached;

FIG. 1.4; Sepals, receptacle, and pedicel;

FIG. 1.5; Bare stem exhibiting thorns, and bare stem showing the flower buds buds, shape of receptacles, and attachment peduncles;

FIG. 1.6; Leaves.

DETAILED DESCRIPTION OF THE VARIETY

Figures 11, 12, 13, 14, 15, 16:
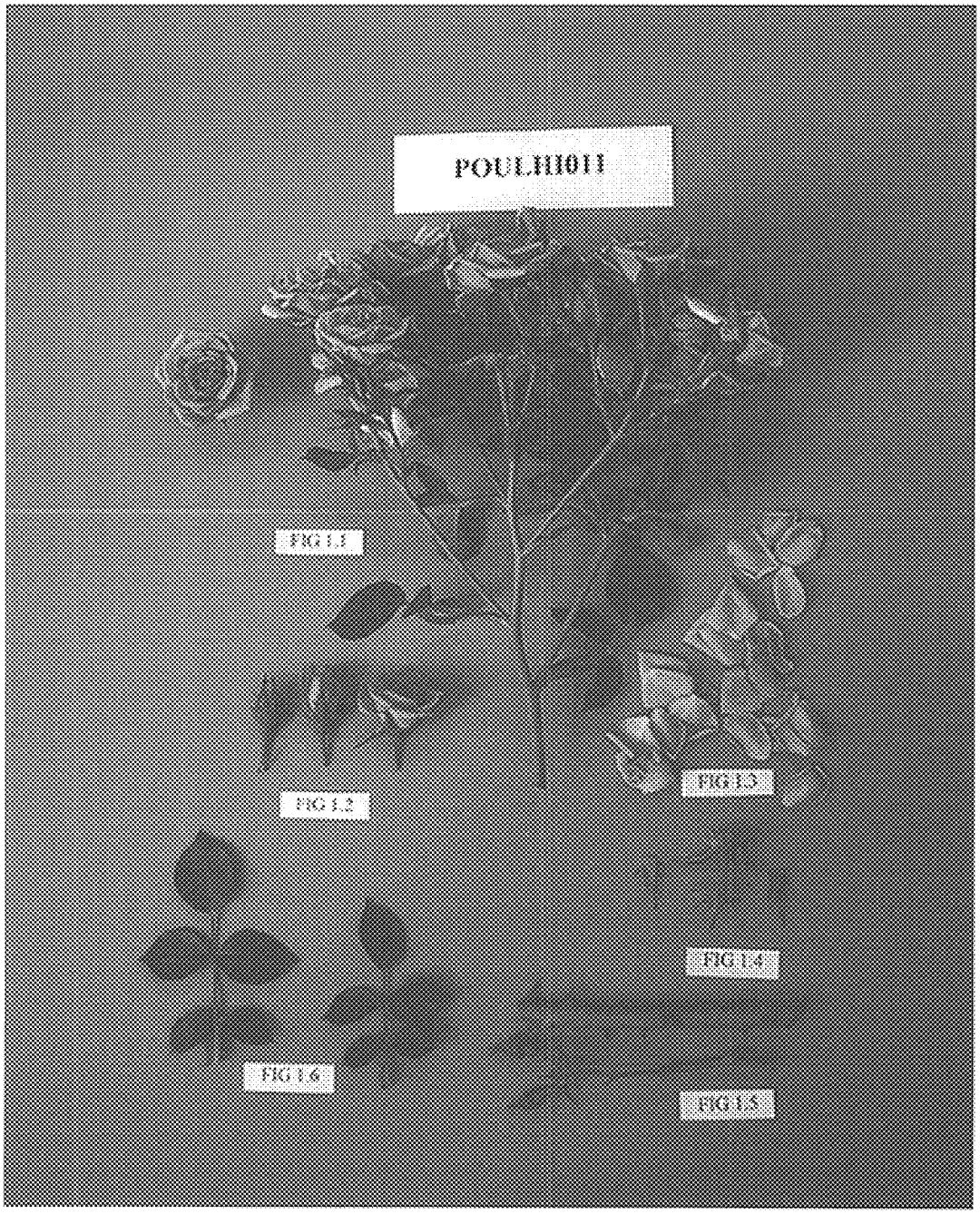

The following is a description of 'POULhi011', as observed in its growth in glasshouses in Fredensborg, Denmark. Observed plants were grown in 15 cm pots, for a period of 3 months. Color references are made using The Royal Horticultural Society (London, England) Colour Chart, 1995, except where common terms of color are used.

For a comparison, several physical characteristics of the rose variety 'POULarbso', a rose variety from the same inventors described and illustrated in U.S. Plant patent application Ser. No. 10/136,452 filed Apr. 29, 2002, now abandoned, are compared to 'POULhi011' in Chart 1.

CHART 1

| | 'POULhi011' | 'POULarbso' |
|---|---|---|
| Flower diameter when open. | 30 mm. | 45 mm to 55 mm. |
| Flower bud size. | Upon opening, 18 mm in length from base of receptacle to end of bud. | Upon opening, 19 mm in length from base of receptacle to end of bud. |

CHART 1-continued

| | 'POULhi011' | 'POULarbso' |
|---|---|---|
| Color of Upper Surface of Flower Petal On Open Flower. | Red-Purple Group 62B. | Red Group 48C. |

FLOWER AND FLOWER BUD

Booming habit: Continuous.

Flower bud:

*Size.*—Upon opening, 18 mm in length from base of receptacle to end of bud.

*Bud form.*—Pointed ovoid.

*Bud color.*—As sepals unfold, Red Group 55B; Red Group 55B at ¼ opening.

*Sepals.*—Upper Surface: Color: Green Group 133A to 143A. Texture: Smooth with scant stipitate glands and moderately pubescent. Lower Surface: Color: Yellow-Green Group 144A. Anthocyanin Greyed-Red Group 181A. Shape: Sepal apex is cirrhose. Base is flat at union with receptacle. Margins: Margins have medium foliaceous appendages on three of the five sepals. Size: 16 mm (l)×5 mm (w).

*Receptacle.*—Surface: Smooth and glabrous. Shape: Urn-shaped. Size: 4 mm (h)×4 mm (w). Color: Yellow-Green Group 144A. Anthocyanin: Plants grown under high light conditions exhibit anthocyanic pigments the color of Greyed-Red Group 181B.

*Peduncle.*—Surface: Fragrant stipitate glands in medium quantity. Length: 11 mm to 15 mm average length. Color: Yellow-Green Group 144B. Strength: Weak.

*Borne.*—In large clusters or cymes. 7 flower buds per individual stem on average.

Flower bloom:

*Fragrance.*—None.

*Duration.*—The blooms have a duration on the plant of approximately 10 to 14 days. Petals fall cleanly away from plant.

*Size.*—Average flower diameter is 30 mm when open.

*Form.*—General shape is a shallow cup.

*Shape of flower when viewed from the side.*—Upon opening, upper part: Flat. Upon opening, lower part: Flat. Open flower, upper part: Convex. Open flower, lower part: Convex.

*Petalage.*—On average 30 petals under normal conditions with 5 petaloids.

Color:

*Upon opening, petals.*—Outermost petals: Outer Side: Red-Purple Group 62A. Inner Side: Red-Purple Group 62B. Innermost petals: Outer Side: Red-Purple Group 62A. Inner Side: Red-Purple Group 62B.

*Upon opening, basal petal spots.*—No distinctive coloration at petal base observed.

*After opening, petals.*—Outermost petals: Outer Side: Red-Purple Group 62A. Inner Side: Red-Purple Group 62B. Innermost petals: Outer Side: Red-Purple Group 62A. Inner Side: Red-Purple Group 62B.

*After opening, basal petal spots.*—No distinctive coloration at petal base observed.

General tonality: On open flower Red-Purple Group 62A. No change in the general tonality at the end of the 10th day. Afterwards, general tonality is Red-Purple Group 62C.

Petals:

*Petal reflex.*—Petals reflex strongly.

*Petal margin.*—Entire with medium undulations of margin.

*Shape.*—Generally deltoid to oval. Base: Variable, from rounded to acute. Apex: Round.

*Size.*—18 mm (l)×18 mm (w).

*Thickness.*—Average.

*Arrangement.*—Not formal.

Petaloids:

*Quantity.*—5 on average.

*Size.*—10 mm (l)×4 mm (w).

*Upper surface.*—Red-Purple Group 62B.

*Lower surface.*—Red-Purple Group 62A.

Reproductive organs:

*Pistils.*—Length: 4 mm long. Quantity: 29 (actual count).

*Pollen.*—None observed.

*Anthers.*—Size: 1 mm long. Color: Yellow-Orange Group 13B. Quantity: 55 (actual count).

*Filaments.*—Color: Yellow Group 4A. Length: 4 mm.

*Stigmas.*—Level relative to the length of the filaments and the height of the anthers. Color: Red-Purple Group 63A.

*Styles.*—Color: Red Group 51B.

*Seed formation.*—Not observed.

PLANT

Plant growth: Vigorous, compact. When grown as a nursery plant on its own roots the average plant height is 40 mm to 60 cm and the average plant width is 45 cm.

Stems:

*Color.*—Young wood: Yellow-Green Group 144A. Older wood: Yellow-Green Group 144A.

*Surface texture.*—Young wood: Smooth. Older wood: Smooth.

Thorns:

*Incidence.*—10 thorns per 10 cm of stem.

*Size.*—Average length: 8 mm.

*Color.*—Greyed-Orange Group 165C.

*Shape.*—Deeply concave to concave.

Plant foliage: Normal number of leaflets on normal leaves in middle of the stem: 5 leaflets.

*Compound leaf size.*—80 mm (l)×55 mm (w).

*Color.*—Juvenile foliage: Upper Leaf Surface: Yellow-Green Group 146A. Lower Leaf Surface: Yellow-Green Group 146B. Mature foliage: Upper Leaf Surface: Yellow-Green Group 146A. Lower Leaf Surface: Yellow-Green Group 146B.

Plant leaves and leaflets:

*Stipules.*—Size: 20 mm in length. Margins: Finely serrated with few stipitate glands. Color: Yellow-Green Group 144A.

*Petiole.*—Length: 20 to 25 mm. Color: Yellow-Green Group 144A. Anthocyanin: None. Underneath: Somewhat pubescent.

*Rachis.*—Size: 35 mm. Color: Yellow-Green Group 144A. Underneath: Somewhat pubescent.

*Leaflet.*—Size: 20 to 25 mm (l)×11 to 20 mm (w). Edge: Finely serrated. Shape: Generally ovate. Leaflet apex is cuspidate. Base is rounded. Texture:

Smooth. Arrangement: Odd pinnate. Venation: Reticulate. Leaf Gloss: Moderately glossy.

Disease resistance: Average resistance to mildew, black spot, and Botrytis under normal growing conditions in Fredensborg, Denmark.

We claim:

1. A new and distinct variety of rose plant of the miniature class, substantially as herein illustrated and described as a distinct and novel rose variety due to its abundant, pink flowers, vigorous growth, compact habit, suitability for production from softwood cuttings in pots, and durable flowers and foliage which make the variety suitable for distribution in the floral industry.

* * * * *

POULH1011